US012569338B2

(12) United States Patent
Smith et al.

(10) Patent No.: US 12,569,338 B2
(45) Date of Patent: Mar. 10, 2026

(54) DILATING INTRODUCER DEVICES AND METHODS FOR VASCULAR ACCESS

(71) Applicant: Laplace Interventional Inc., Plymouth, MN (US)

(72) Inventors: Nathaniel Thomas Smith, Saint Paul, MN (US); Gunnar Paul Askegaard, Maple Grove, MN (US); Lucas Tradd Schneider, Champlin, MN (US); Ramji Iyer, Plymouth, MN (US)

(73) Assignee: Laplace Interventional Inc., Plymouth, MN (US)

( * ) Notice: Subject to any disclaimer, the term of this patent is extended or adjusted under 35 U.S.C. 154(b) by 36 days.

(21) Appl. No.: 18/618,072

(22) Filed: Mar. 27, 2024

(65) Prior Publication Data

US 2025/0090196 A1 Mar. 20, 2025

Related U.S. Application Data

(62) Division of application No. 18/369,568, filed on Sep. 18, 2023, now Pat. No. 11,969,188.

(51) Int. Cl.
| | |
|---|---|
| *A61B 17/34* | (2006.01) |
| *A61F 2/24* | (2006.01) |
| *A61M 25/09* | (2006.01) |
| *A61M 29/02* | (2006.01) |

(52) U.S. Cl.
CPC ........ *A61F 2/2427* (2013.01); *A61B 17/3421* (2013.01); *A61M 25/09041* (2013.01)

(58) Field of Classification Search
CPC ............ A61M 29/02; A61M 25/09041; A61M 25/0668; A61M 2025/0675; A61F 2/2436;

A61B 17/3421; A61B 17/3439; A61B 17/3423; A61B 17/0482; A61B 17/0483; A61B 2017/06052; A61B 17/02

See application file for complete search history.

(56) References Cited

U.S. PATENT DOCUMENTS

| | | | |
|---|---|---|---|
| 4,350,151 A | 9/1982 | Scott | |
| 6,017,362 A | 1/2000 | Lau | |
| 6,090,072 A | 7/2000 | Kratoska et al. | |
| 6,623,460 B1 * | 9/2003 | Heck ..................... | A61M 39/06 604/256 |
| 7,713,193 B2 | 5/2010 | Nance et al. | |
| 8,282,664 B2 | 10/2012 | Nance et al. | |
| 8,562,559 B2 | 10/2013 | Bishop et al. | |
| 8,728,153 B2 | 5/2014 | Bishop et al. | |
| 8,790,387 B2 | 7/2014 | Nguyen et al. | |

(Continued)

OTHER PUBLICATIONS

International Search Report and Written Opinion in International Appln. No. PCT/US2024/046155, mailed on Sep. 25, 2024, 6 pages.

*Primary Examiner* — Sarah W Aleman
*Assistant Examiner* — Mikail A Mannan
(74) *Attorney, Agent, or Firm* — Fish & Richardson P.C.

(57) ABSTRACT

Devices used to deploy transvascular medical device systems and methods for using such devices are described in this document. For example, this document describes dilating introducer devices used for the percutaneous vascular deployment of catheter-based medical devices such as structural heart medical devices. Such dilating introducer devices can facilitate the percutaneous vascular deployment of catheter-based medical devices without an additional introducer sheath.

6 Claims, 12 Drawing Sheets

(56)                References Cited

U.S. PATENT DOCUMENTS

| | | |
|---|---|---|
| 8,845,712 B2 | 9/2014 | Irwin et al. |
| 9,192,751 B2 | 11/2015 | Macaulay et al. |
| 9,301,840 B2 | 4/2016 | Nguyen et al. |
| 9,301,841 B2 | 4/2016 | Nguyen et al. |
| 9,320,508 B2 | 4/2016 | Carroux |
| 9,433,766 B2 | 9/2016 | Bishop et al. |
| 9,555,214 B2 | 1/2017 | Ren et al. |
| 9,801,657 B2 | 10/2017 | Furnish et al. |
| 9,987,134 B2 | 6/2018 | Nguyen et al. |
| 10,391,279 B2 | 8/2019 | Zhou et al. |
| 10,391,280 B2 | 8/2019 | Zhou et al. |
| 10,391,281 B2 | 8/2019 | Zhou et al. |
| 10,398,469 B2 | 9/2019 | Coyle et al. |
| 10,499,895 B2 | 12/2019 | Anderson |
| 10,500,377 B2 | 12/2019 | Zhou et al. |
| 10,517,720 B2 | 12/2019 | Nguyen et al. |
| 10,524,905 B2 | 1/2020 | Nguyen et al. |
| 10,524,906 B2 | 1/2020 | Nguyen et al. |
| 10,524,907 B2 | 1/2020 | Nguyen et al. |
| 10,543,342 B2 | 1/2020 | Obradovic |
| 10,548,631 B2 | 2/2020 | Fitterer et al. |
| 10,639,152 B2 | 5/2020 | Le et al. |
| 10,716,919 B2 | 7/2020 | Zhou et al. |
| 10,792,150 B2 | 10/2020 | Nguyen et al. |
| 10,792,471 B2 | 10/2020 | Zhou et al. |
| 10,799,685 B2 | 10/2020 | Zhou et al. |
| 10,850,064 B2 | 12/2020 | Willard et al. |
| 10,918,829 B2 | 2/2021 | Fitterer et al. |
| 10,980,569 B2 | 4/2021 | Fitterer et al. |
| 11,045,317 B2 | 6/2021 | Nguyen et al. |
| 11,246,581 B2 | 2/2022 | Anderson |
| 11,406,796 B2 | 8/2022 | Zhou et al. |
| 11,420,026 B2 | 8/2022 | Zhou et al. |
| 11,564,710 B2 | 1/2023 | Fitterer et al. |
| 2015/0025312 A1* | 1/2015 | de Canniere .......... A61B 1/018 |
| | | 600/104 |
| 2018/0344987 A1* | 12/2018 | Lancette ........... A61M 25/0668 |
| 2019/0192273 A1* | 6/2019 | Debus ................... A61F 2/064 |
| 2020/0038643 A1* | 2/2020 | Bierman .......... A61M 25/0662 |
| 2023/0191088 A1 | 6/2023 | Blanchard |
| 2024/0058034 A1* | 2/2024 | Cortez, Jr. ....... A61B 17/00234 |

* cited by examiner

120

124b

124a

122

120

124a

124b

126a

126b

122

DILATING INTRODUCER DEVICES AND METHODS FOR VASCULAR ACCESS

CROSS-REFERENCE TO RELATED APPLICATIONS

This application claims the benefit of U.S. application Ser. No. 18/369,568 filed Sep. 18, 2023. The disclosure of the prior application is considered part of (and is incorporated by reference in) the disclosure of this application.

BACKGROUND

1. Technical Field

This document relates to devices used to deploy transvascular medical device systems and methods for using such devices. For example, this document relates to dilating introducer devices used for the percutaneous vascular deployment of catheter-based medical devices such as structural heart medical devices.

2. Background Information

Percutaneous sheath introducer devices are intended for use in settings such as the hospital catheterization laboratory for the percutaneous introduction of various medical devices into veins and/or arteries in a variety of diagnostic and therapeutic procedures.

Dilators are tubular devices used for dilating the percutaneous opening into a blood vessel. It has tapered distal end and proximal end comprising a hub.

SUMMARY

This document describes devices used to deploy transvascular medical device systems and methods for using such devices. For example, this document describes dilating introducer devices used for the percutaneous vascular deployment of catheter-based medical devices such as structural heart medical devices. Such dilating introducer devices can facilitate the percutaneous vascular deployment of catheter-based medical devices without an additional introducer sheath.

In one aspect this disclosure is directed to a dilating introducer device includes a conical tube comprising a first half releasably coupled to a second half; a clip releasably coupled to the first and second halves of the conical tube; and a suture removably extending through: (i) a first opening defined by the first half and (i) a first opening defined by the second half.

Such a dilating introducer device may optionally include one or more of the following optional features. In some embodiments, the suture extends through a first opening defined by the clip. In some such embodiments, the suture extends through a second opening defined by the clip. The suture may extend through: (i) a second opening defined by the first half and (i) a second opening defined by the second half. In some embodiments, the suture extends within a lumen of the conical tube between: (i) the first and second openings defined by the first half and (ii) the first and second openings defined by the second half. The first openings defined by the first and second halves may be at a tip portion of the conical tube. In some embodiments, the suture extends around an exterior of the conical tube between the first openings defined by the first and second halves of the conical tube. The clip may define an open-ended slot. The conical tube may include a hub that is releasably coupled in the open-ended slot. In some embodiments, the clip is flexible and is removable from the first and second halves of the conical tube by flexure of the clip. The first and second halves of the conical tube may be identical to each other. A guidewire opening may be defined at a distal-most tip of the conical tube. In some embodiments, the first and second halves of the conical tube comprise a plurality of protrusions and a plurality of complimentary recesses that releasably couple the first and second halves together.

In another aspect, this disclosure is directed to a method of introducing a catheter-based medical device into a blood vessel of a patient, the method comprising: (i) inserting a needle into the patient until a distal end portion of the needle is positioned in the blood vessel; (ii) insert a guidewire through the needle and into the blood vessel; (iii) removing the needle from the blood vessel; (iv) advancing a dilating introducer over the guidewire until a distal end portion of the dilating introducer is in the blood vessel, wherein at least a portion of the catheter-based medical device is in a lumen of the dilating introducer during the advancing; (v) advancing the catheter-based medical device through the lumen of the dilating introducer into the vessel; and (vi) removing the dilating introducer from the blood vessel.

Such a method may optionally include one or more of the following features. The removing the dilating introducer from the blood vessel may comprise longitudinally splitting the dilating introducer into multiple pieces. The removing the dilating introducer from the blood vessel may comprise removing a suture from engagement with the dilating introducer prior to the longitudinally splitting the dilating introducer into multiple pieces. In some embodiments, the method is performed without using a conventional introducer sheath. In particular embodiments, a distal end portion of the catheter-based medical device is in the vessel prior to the removing the dilating introducer from the blood vessel. The catheter-based device may be a prosthetic heart valve coupled on a system of delivery catheters. The dilating introducer may be conically shaped.

Particular embodiments of the subject matter described in this document can be implemented to realize one or more of the following advantages. In some embodiments, various heart conditions such as valvular disease, cardiac fibrillation, diastolic heart failure and others can be treated using the devices and methods provided herein.

In some embodiments, various heart conditions can be treated in a minimally invasive fashion using the devices and methods provided herein. Such minimally invasive techniques can reduce recovery times, patient discomfort, and treatment costs.

The devices and methods described herein are designed and optimized to improve procedural efficiencies, costs, and patient outcomes in comparison to conventional methods that use multiple devices (such as a dilator and a separate introducer sheath) to perform the functions of the combined dilator and introducer as described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices used to deploy transvascular medical device systems and methods for using such devices. For example, this document describes dilating introducer devices used for the percutaneous vascular deployment of catheter-based medical devices such as, but not limited to, structural heart medical devices. Such dilating introducer devices can facilitate the percutaneous vascular deployment of catheter-based medical devices without an additional introducer sheath.

A conventional percutaneous introduction of a transvascular medical device typically includes the following steps:

i) Percutaneous needle introduction into the blood vessel with the needle defining a lumen through which a guidewire is introduced into the blood vessel.

ii) Then, the needle is retracted, leaving the guidewire in place.

iii) Then, an introducer sheath along with a dilator inside its lumen is introduced over the guidewire.

iv) The dilator is then removed with the introducer sheath and guidewire remaining in place. At this instance, the introducer has a seal at the proximal end (handle) which creates a seal over the guidewire.

a. This seal is critical and if not proper, can result in air being introduced into the blood vessel or loss of a significant amount of blood.

b. The effectiveness of the seal may be affected by the difference between the inner diameter of the introducer and the outer diameter of the guidewire (typically 0.014" or 0.035"). The higher this difference, the engineering complexity of the achieving a proper seal is higher. This is especially pertinent in case of large transvascular medical devices that are:

i. 10Fr-20Fr: Transvascular medical device systems such as transcatheter aortic valve replacement, left atrial appendage closure devices, RF ablation catheters for A-Fib treatments, etc.

ii. 24Fr-40Fr: Transvascular medical device systems such as transcatheter mitral repair, transcatheter mitral replacement, transcatheter tricuspid repair, transcatheter tricuspid replacement, etc.

v) The transvascular medical device is then introduced through the introducer sheath over the guidewire. The seal (discussed in iv.b.ii above) should not only be effective between the introducer and the guidewire, but also be effective when a 10Fr-40Fr transvascular medical device is being introduced.

The dilating introducers described herein combine steps iii, iv, and v, and therefore reduces the number of steps. The dilating introducers described herein also ensure that there are no instances in the procedure where the risk of air introduction and/or blood loss is high. As such, it allows for a safer procedure. The dilating introducers described herein also allow for fewer devices and therefore could be more inexpensive.

Figures 1, 2:
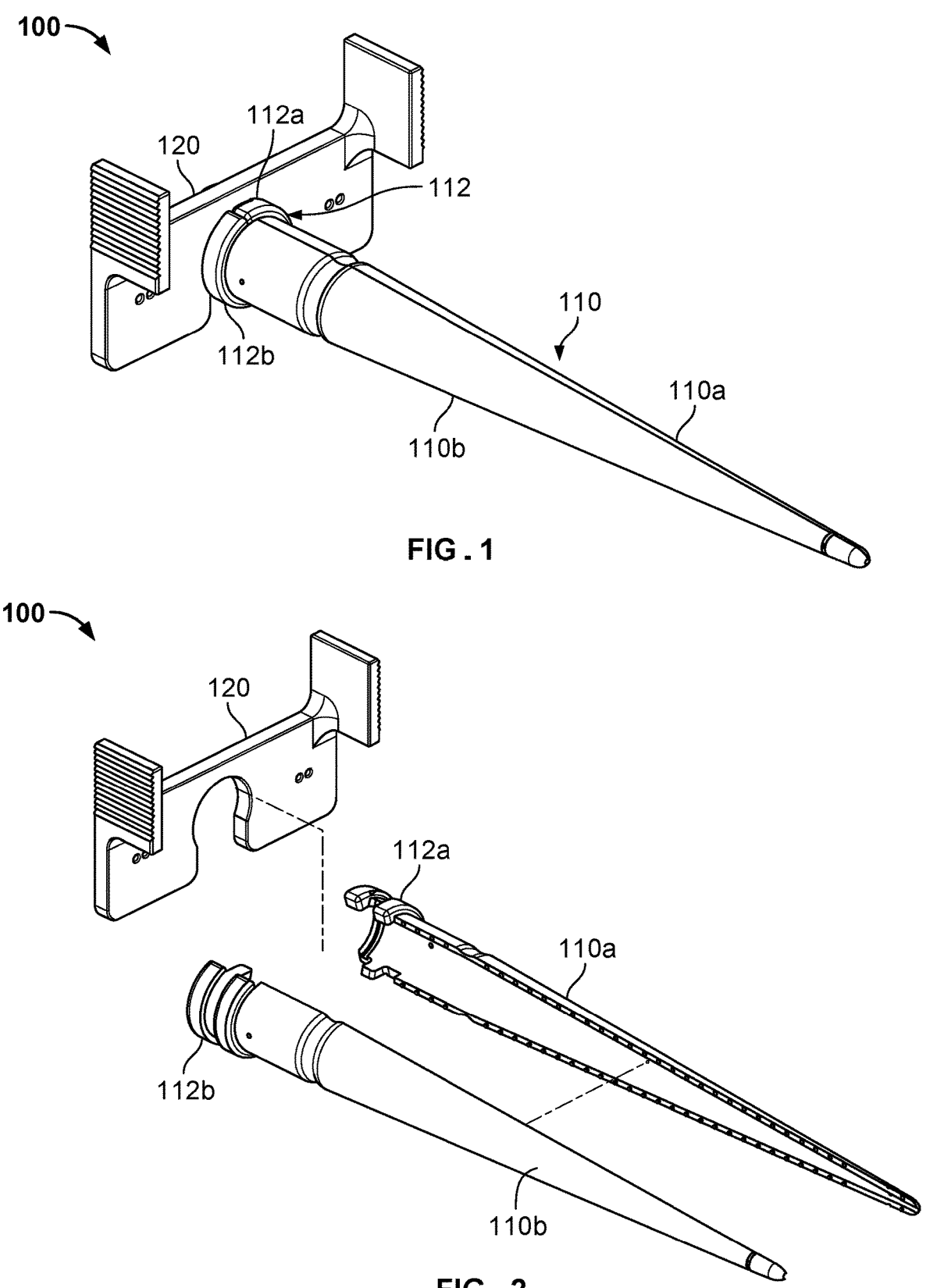
FIG. 1 is a perspective view of an example vascular dilating introducer device in accordance with some embodiments provided herein.
FIG. 2 is an exploded perspective view of the vascular dilating introducer device of FIG. 1.

FIG. 1 illustrates an example percutaneous introducer and vascular dilator device 100 (or "dilating introducer 100" for short) in accordance with some embodiments described herein. As described further below (e.g., FIGS. 10-23), the dilating introducer 100 can be used by a medical clinician to percutaneously insert a transvascular medical device system into a blood vessel of a patient. The dilating introducer 100 serves to both dilate the tissue opening and/or blood vessel and also to introduce the transvascular medical device system into the blood vessel through the dilating introducer 100. That is, the dilating introducer 100 is a multifunctional device that can eliminate the need for a conventional introducer sheath that is commonly used when percutaneously inserting a transvascular medical device system into a blood vessel of a patient.

The dilating introducer 100 includes a conical tube 110 and a clip 120 that is releasably coupleable to, or on, the conical tube 110. In particular, the clip 120 is releasably coupleable to a hub 112 located at a proximal end of the conical tube 110. Even more particularly, in the depicted embodiment the clip 120 is releasably coupleable to the hub 112 by seating the clip 120 in an annular recess defined by the hub 112.

Also referring to FIG. 2, in the depicted embodiment the conical tube 110 is made of two halves, a first half 110a and a second half 110b. In other words, it can be said that the conical tube 110 is a two-part conical tube 110 that is made to be splitable (which serves a useful purpose when introducing a transvascular medical device system into a blood vessel of a patient, as described further below). The hub 112 is also made of two halves, a first hub portion 112a and a second hub portion 112b.

In the depicted embodiment, the two halves 110a/112a and 110b/112b that make up the conical tube 110 and hub 112 are identical to each other. That uniformity is advantageous from a manufacturing standpoint. However, it is not required in all embodiments for the conical tube 110 to be made of two identical halves.

Figure 3:
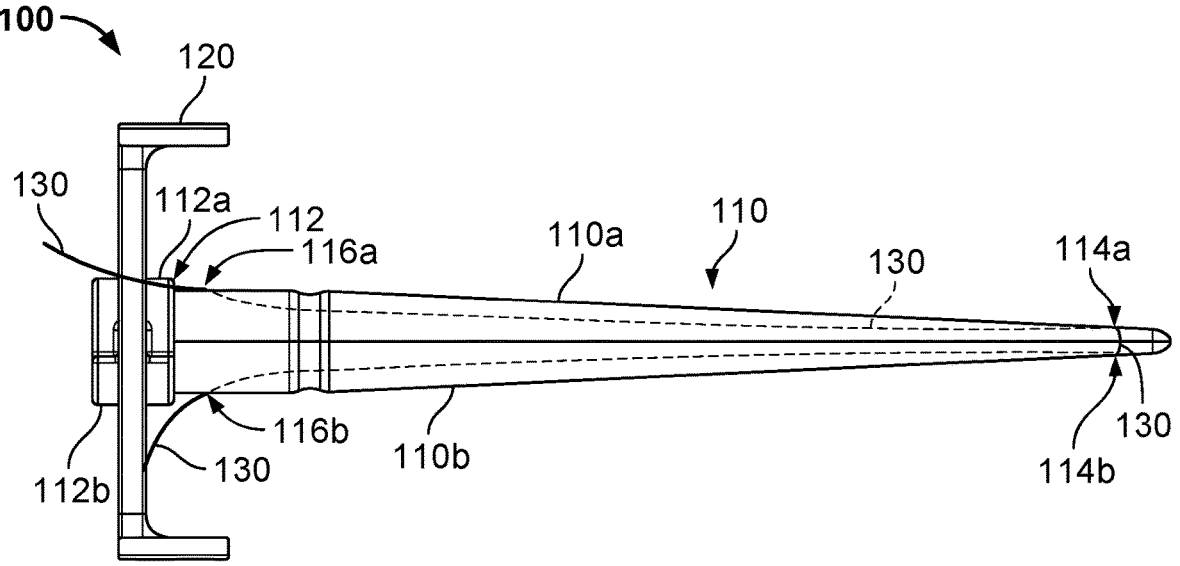
FIG. 3 is a top view of the vascular dilating introducer device of FIG. 1.
Figure 4:
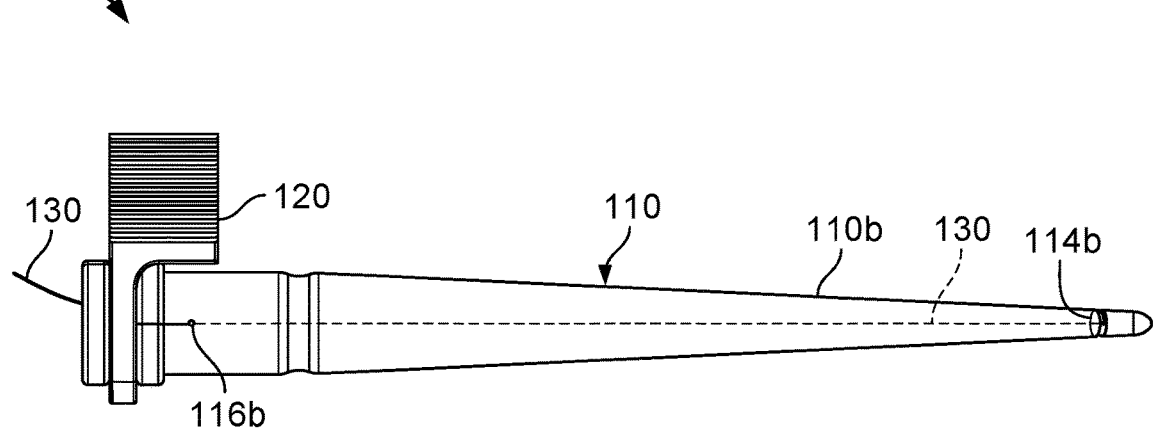
FIG. 4 is a side view of the vascular dilating introducer device of FIG. 1.

Referring also to FIGS. 3 and 4, the dilating introducer 100 also includes a suture 130. The suture 130 is removably coupled with the conical tube 110 and with the clip 120. The suture 130 serves to maintain the first half 110a and the second half 110b of the conical tube 110 in a coupled arrangement as depicted. In particular, the suture 130 serves to hold the distal tip portions of the first half 110a and the second half 110b in engagement with each other, while the clip 120 serves to hold the proximal portions of the first half 110a and the second half 110b in engagement with each other. However, when it is desired to allow the dilating introducer 100 to split when advancing a transvascular medical device system therethrough, the clip 120 and the suture 130 can be partially or fully removed from engagement with the conical tube 110. When removed, the clip 120 will no longer hold the proximal portions of the first half 110a and the second half 110b in engagement with each other, and the suture 130 will no longer hold the distal tip portions of the first half 110a and the second half 110b of the conical tube 110 in engagement with each other. In that case, the first half 110a and the second half 110b of the conical tube 110 can be split apart from each other.

Figure 5:
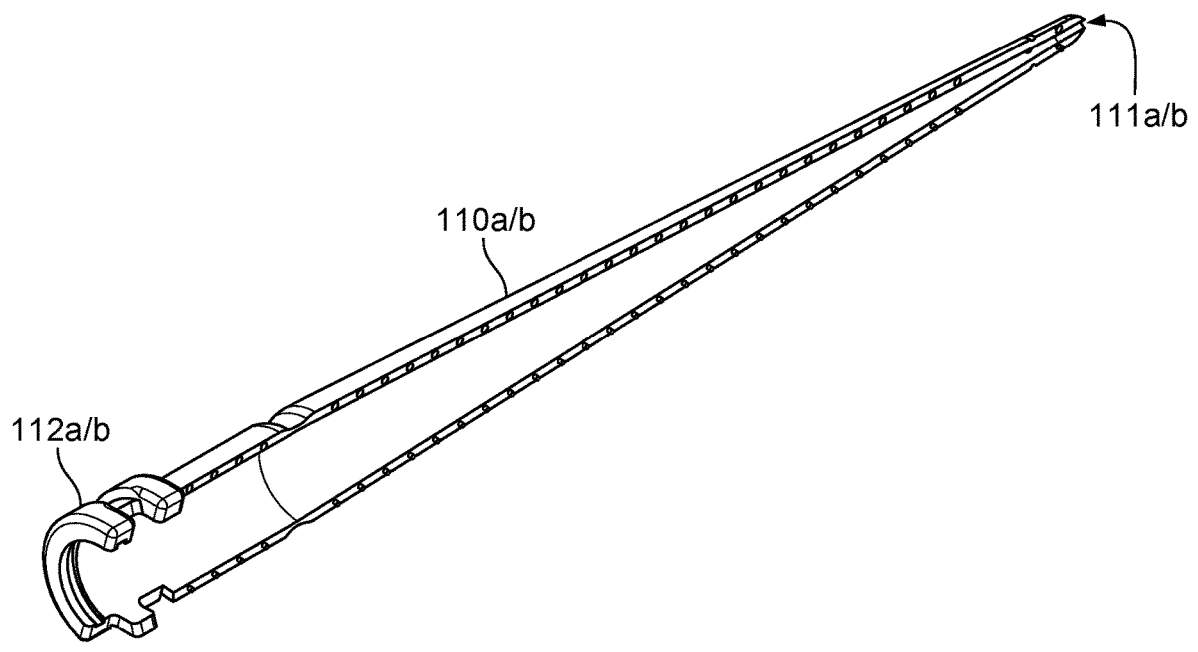
FIG. 5 is a perspective view of a half conical tube of the vascular dilating introducer device of FIG. 1.
Figure 6:
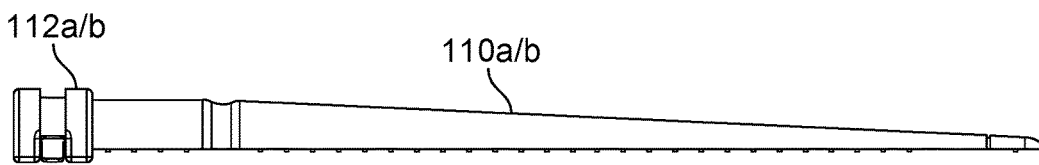
FIG. 6 is a top view of the half conical tube of FIG. 5.
Figure 7:
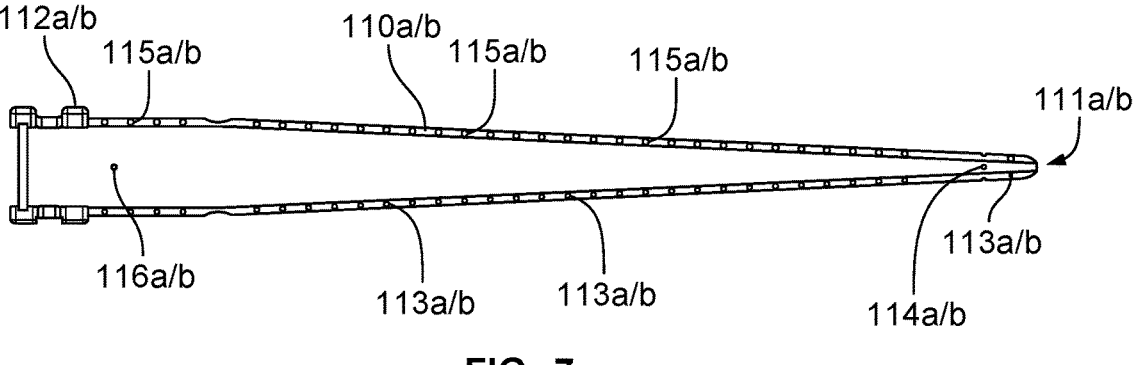
FIG. 7 is a side view of the half conical tube of FIG. 5.

Referring also to FIGS. 5-7, it can be seen (particularly in FIG. 7) that the conical tube halves 110a/b each define a first opening 114a/b and a second opening 116a/b through a wall of the conical tube halves 110a/b. The openings 114a/b and 116a/b allow the suture 130 to pass therethrough. Accordingly, the suture 130 can be releasably coupled with the conical tube 110 by threading it through the openings 114a/b and 116a/b in a particular orientation or pattern.

For example, in the depicted embodiment the suture 130 extends from the clip 120 and passes into the lumen defined by the conical tube 110 through the second opening 116a. Then the suture 130 extends distally and longitudinally in the lumen along the conical half 110a to the distal tip portion of the conical tube 110 where it exits the lumen through the first opening 114a. After exiting the lumen through the first opening 114a, the suture 130 wraps 180° around the outside of the distal tip portions of the conical tube halves 110a/b, and then reenters the lumen through the first opening 114b. From the distal end portion of the lumen, the suture extends proximally and longitudinally in the lumen along the conical half 110b until it exits the lumen through the second opening 116b. After exiting the second opening 116b, the suture 130 again extends to the clip 120.

Adding tension to the suture 130 will hold the distal tip portions of the conical tube halves 110a/b securely together. In the depicted embodiment, the suture 130, as it extends between the first opening 114a and the first opening 114b, resides in an annular groove/recess defined around an outer circumference of the distal tip portions of the conical tube halves 110a/b.

Still referring to FIGS. 5-7, the conical tube halves 110a/b each define a semicircular guidewire opening 111a/b at the distal-most tips of the conical tube halves 110a/b. Accordingly, as described further below, the conical tube 110 can be advanced over a guidewire via the guidewire opening 111a/b.

A series of protrusions 113a/b extend from a first longitudinal wall surface of the each of the conical tube halves 110a/b. In addition, a corresponding series of recesses 115a/b are defined along a second longitudinal wall surface of the each of the conical tube halves 110a/b. Accordingly, when the two conical tube halves 110a/b are mated together to form the conical tube 110, the series of protrusions 113a/b extend into the series of recesses 115a/b. In addition to the suture 130 holding the conical tube halves 110a/b together, this mating arrangement between the protrusions 113a/b and the recesses 115a/b further helps to hold the conical tube halves 110a/b together in the assembled form of the conical tube 110.

Figure 8:
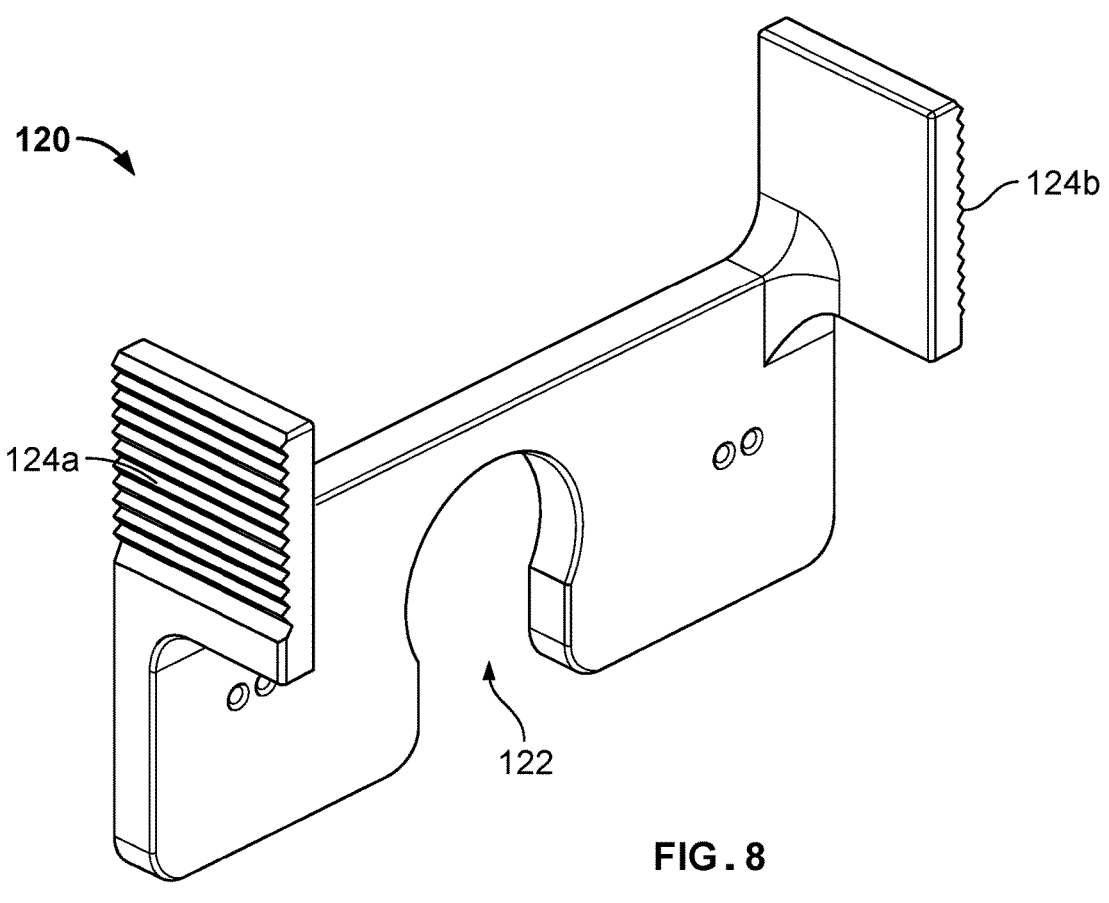
FIG. 8 is a perspective view of a clip of the vascular dilating introducer device of FIG. 1.
Figure 9:
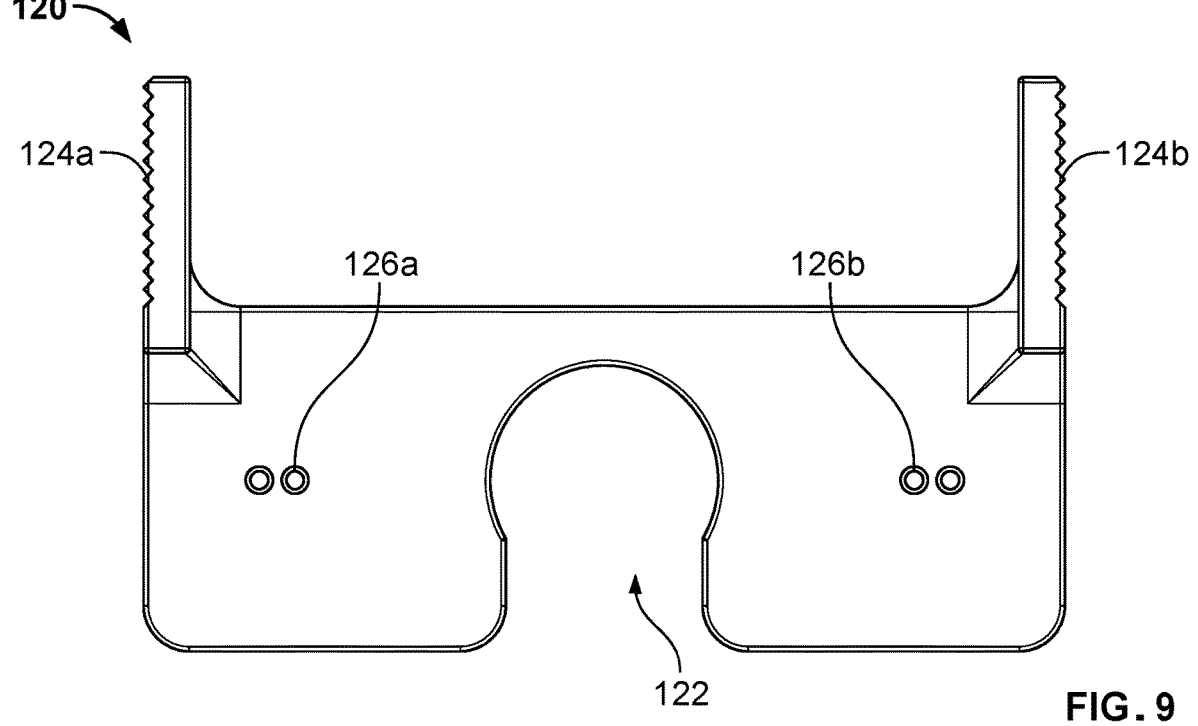
FIG. 9 is a front view of the clip of FIG. 8.

Referring also to FIGS. 8 and 9, the clip 120 defines an open-ended slot 122 in which the hub 112 of the conical tube 110 is slidably received. The clip 120 also includes two opposing finger pads 124a and 124b. When a clinician user desires to uncouple the clip 120 from the hub 112, the clinician user can apply compression force by pinching the two opposing finger pads 124a and 124b to induce flexure of the clip 120 such that the open-ended slot 122 will widen. With the widened open-ended slot 122, the clip 120 can be easily slipped off the hub 112 of the conical tube 110.

The clip 120 also defines one or more first holes 126a and one or more second holes 126b. The one or more first holes 126a and one or more second holes 126b can be used for the suture 130 to extend through and/or to connect the suture 130 to the clip 120 as desired.

FIGS. 10-23 are a series of illustrations that depict how the dilating introducer 100 can be used to both dilate a tissue opening and/or blood vessel and also to introduce a transvascular medical device system into the blood vessel.

Figures 10, 11:
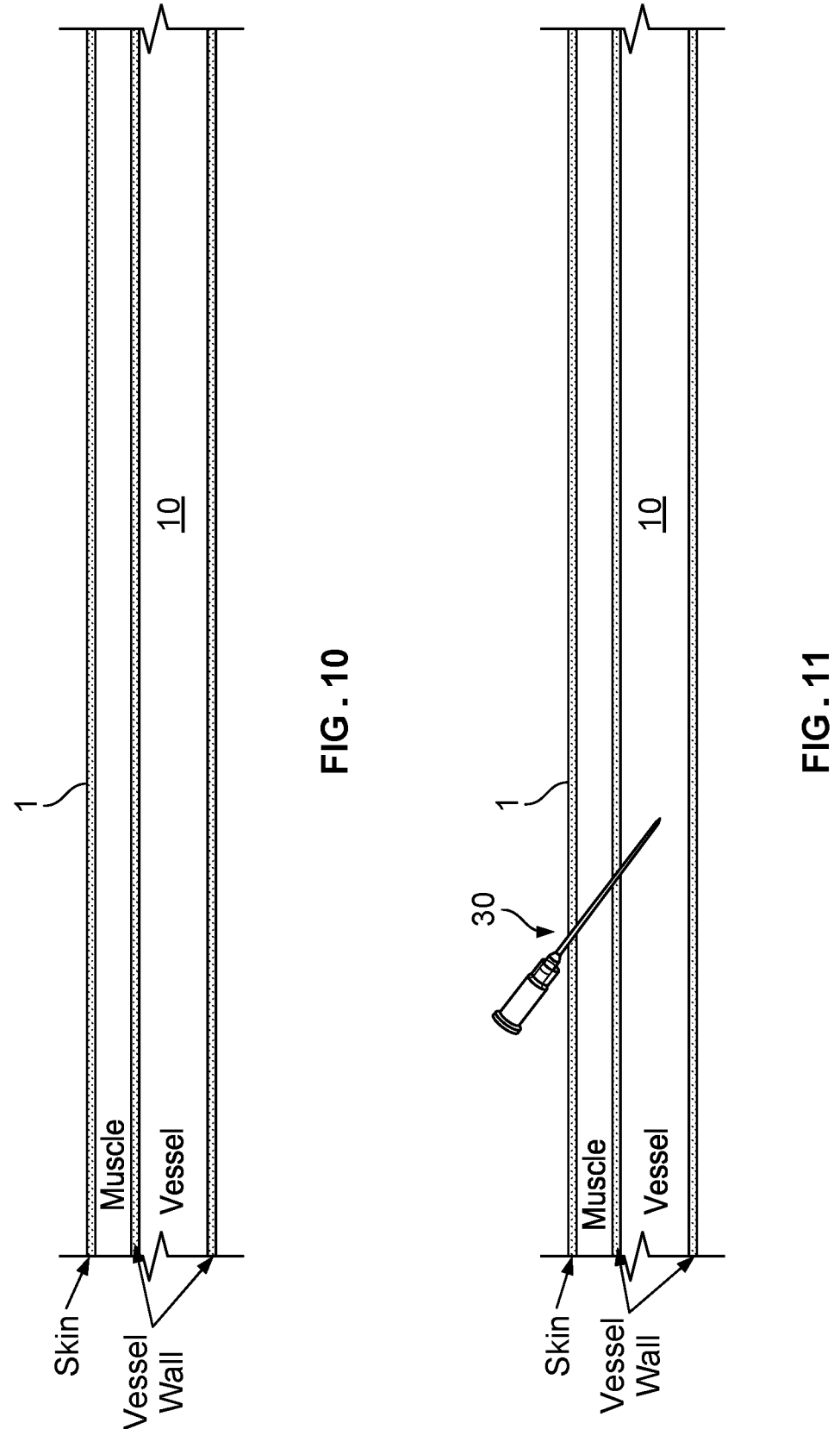
FIG. 10 is a schematic cross-section view of a patient's skin, subcutaneous muscle layer, and blood vessel.
FIG. 11 shows the schematic cross-section view of FIG. 10 with an introducer needle installed by which percutaneous access to the blood vessel is attained.

FIG. 10 shows a cross-sectional view of skin layer 1, a subcutaneous muscle layer, and a blood vessel 10.

In FIG. 11, an introducer needle 30 has been percutaneously inserted such that its distal tip portion is positioned in the blood vessel 10.

Figures 12, 13:
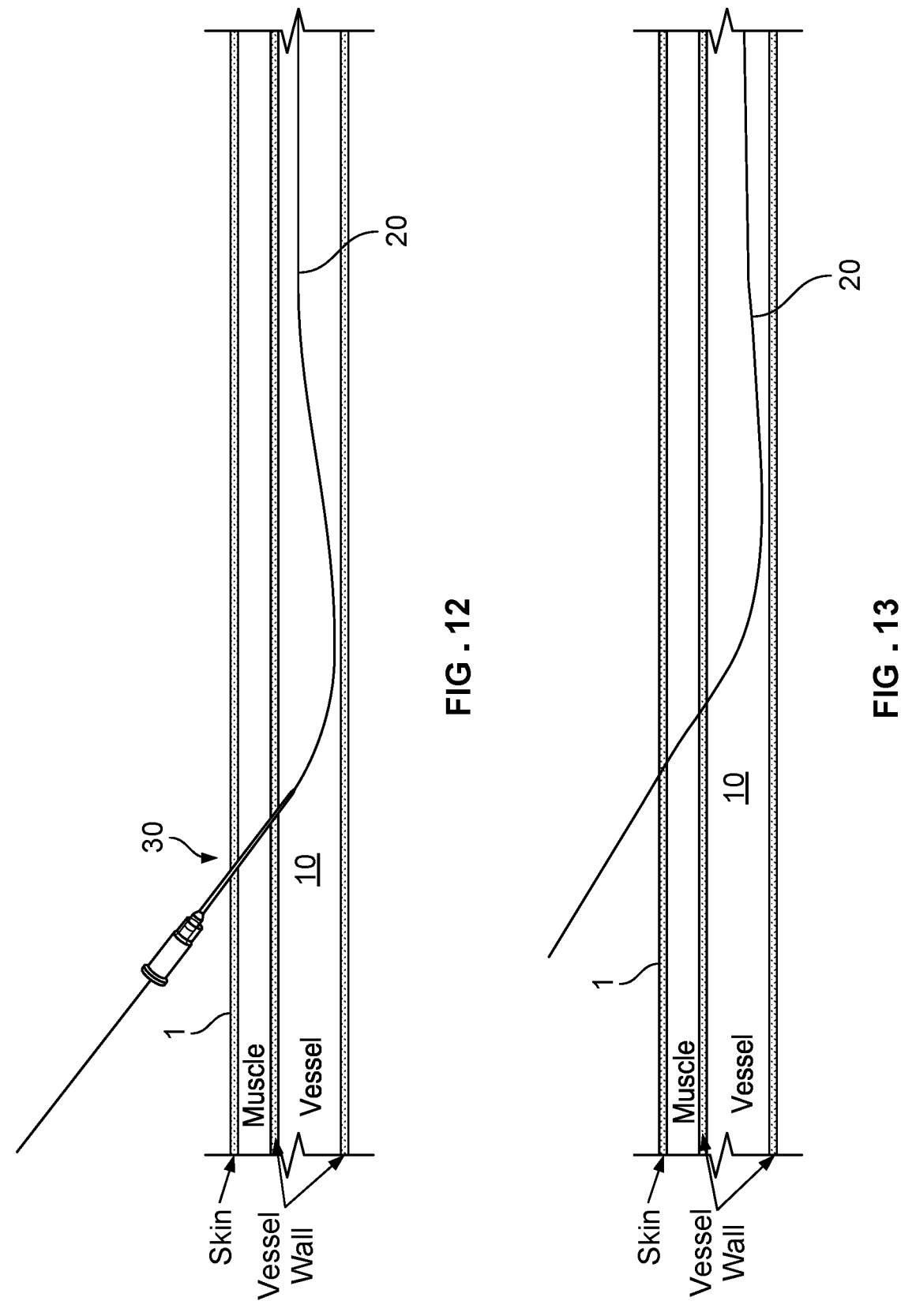
FIG. 12 shows the schematic cross-section view of FIG. 11 with a guidewire installed into the blood vessel via the introducer needle.
FIG. 13 shows the schematic cross-section view of FIG. 12 with the introducer needle removed and the guidewire remaining installed in the blood vessel.

In FIG. 12, a guidewire 20 has been inserted through the lumen of the introducer needle 30 such that the distal end portion of the guidewire 20 is positioned in the blood vessel 10.

In FIG. 13, the introducer needle 30 has been removed and the guidewire 20 is remaining percutaneously extending in the blood vessel 10.

Figures 14, 15:
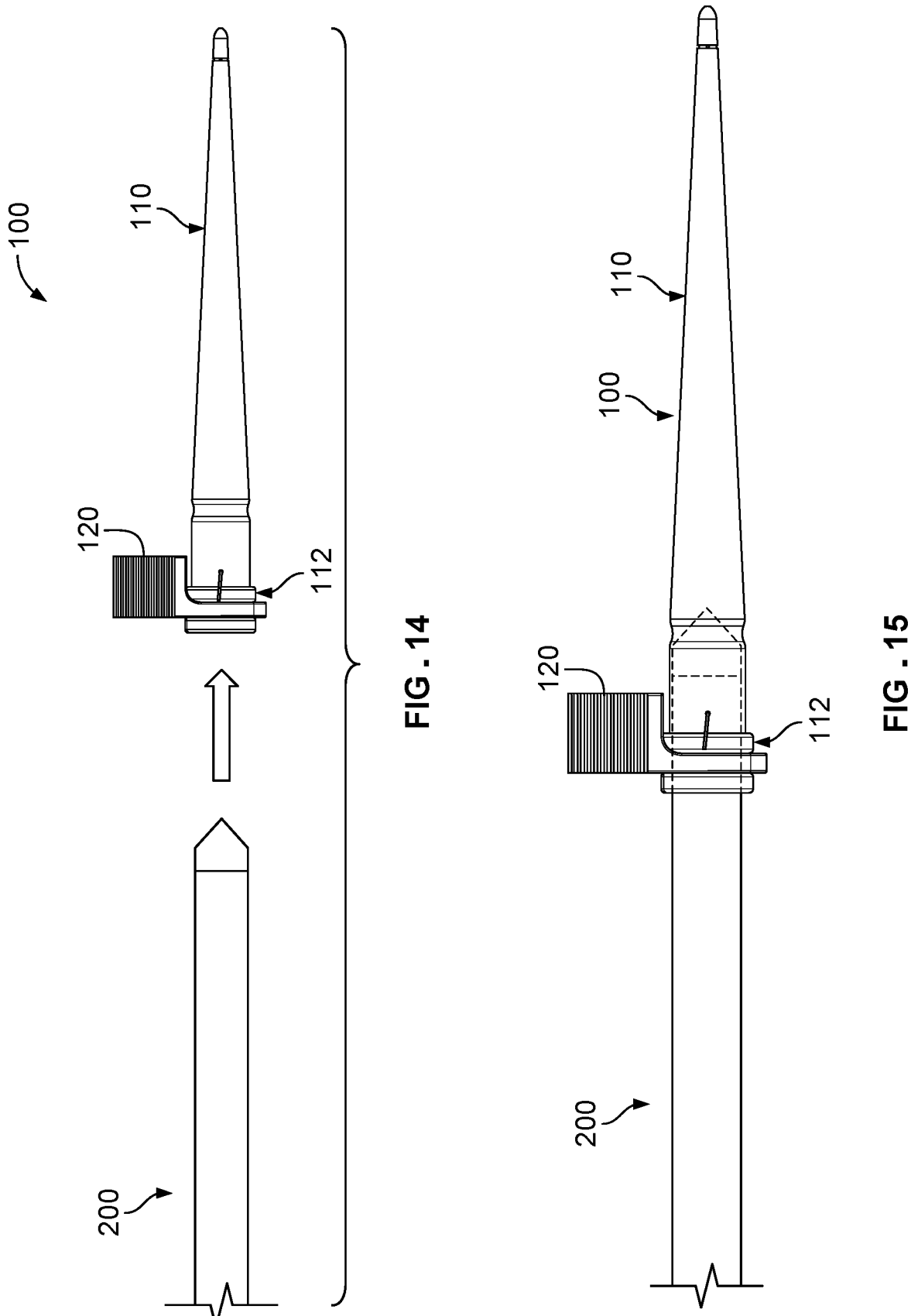
FIG. 14 shows a transvascular medical device system and the vascular dilating introducer device of FIG. 1.
FIG. 15 shows a distal end portion of the transvascular medical device system of FIG. 14 inserted within a proximal end portion of the vascular dilating introducer device of FIG. 1.

FIGS. 14 and 15 illustrate how an example transvascular system 200 can be engaged with the dilating introducer 100. The distal end portion of the transvascular system 200 is positioned in the proximal end portion of the dilating introducer 100 (as shown in FIG. 15). The clip 120 and suture 130 are on the conical tube 110 to hold the two-piece conical tube 110 together as a conical assembly.

The transvascular system 200 represents any type of medical device system that is deployed by advancement, using one or more catheters, along the vascular system of a patient.

Figures 16, 17:
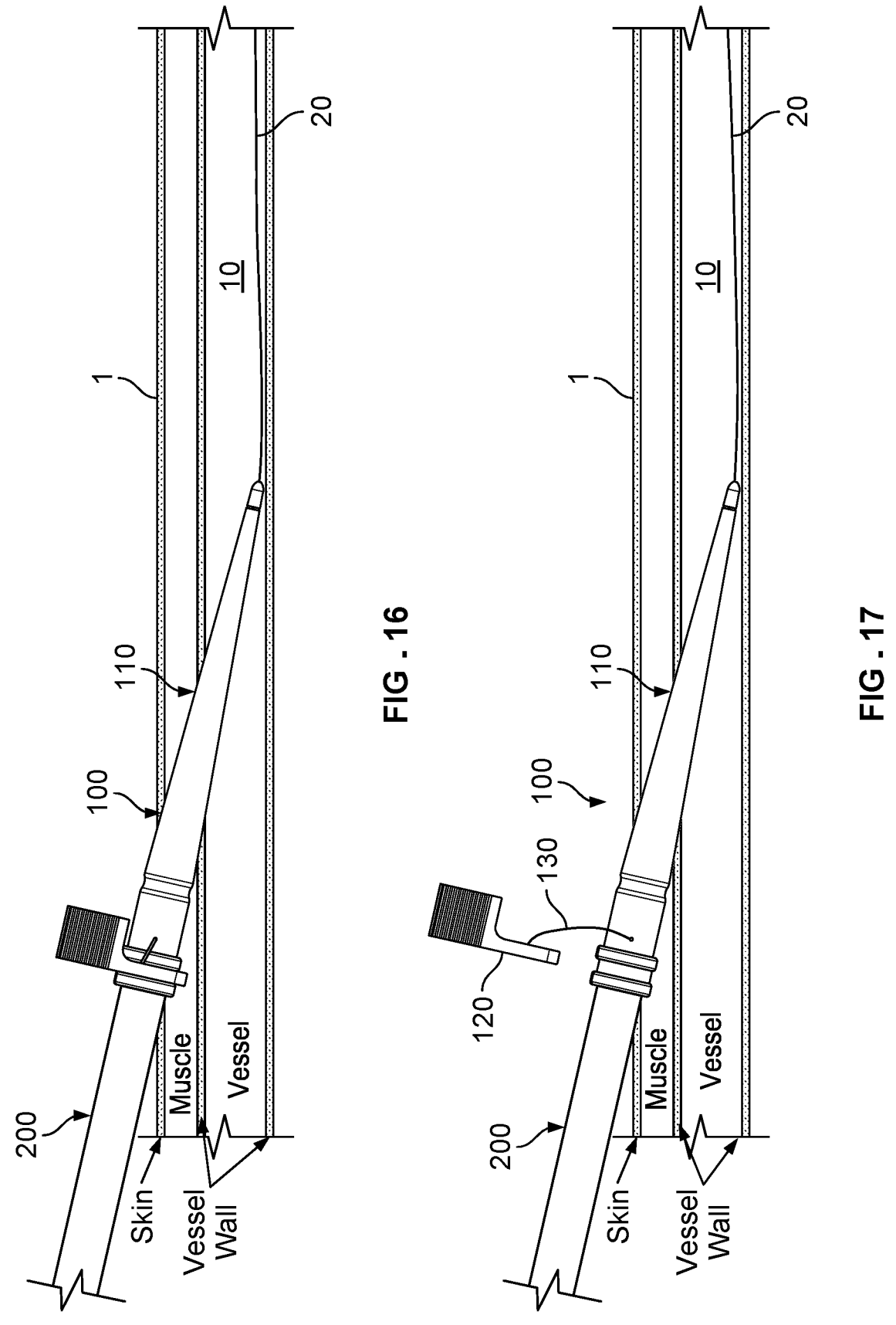
FIG. 16 shows the schematic cross-section view of FIG. 13 with the vascular dilating introducer device and transvascular medical device system of FIG. 15 after being percutaneously inserted into the blood vessel over the guidewire.
FIG. 17 shows the arrangement of FIG. 16 with the clip of the vascular dilating introducer device being removed therefrom.

FIG. 16 shows the dilating introducer 100 (with the transvascular system 200 coupled thereto) after its percutaneous advancement over the guidewire 20. At least the distal tip portion of the dilating introducer 100 is positioned in the blood vessel 10. As the dilating introducer 100 is percutaneously advanced to the depicted position, the dilating introducer 100 dilates (enlarges) the openings of the skin 1, the muscle layer, and the blood vessel 10 in preparation for the later advancement of the transvascular system 200.

FIG. 17 illustrates the removal of the clip 120 and the suture 130 from the two-piece conical tube 110. Accordingly, the two-piece conical tube 110 is now free to longitudinally split apart.

Figures 18, 19:
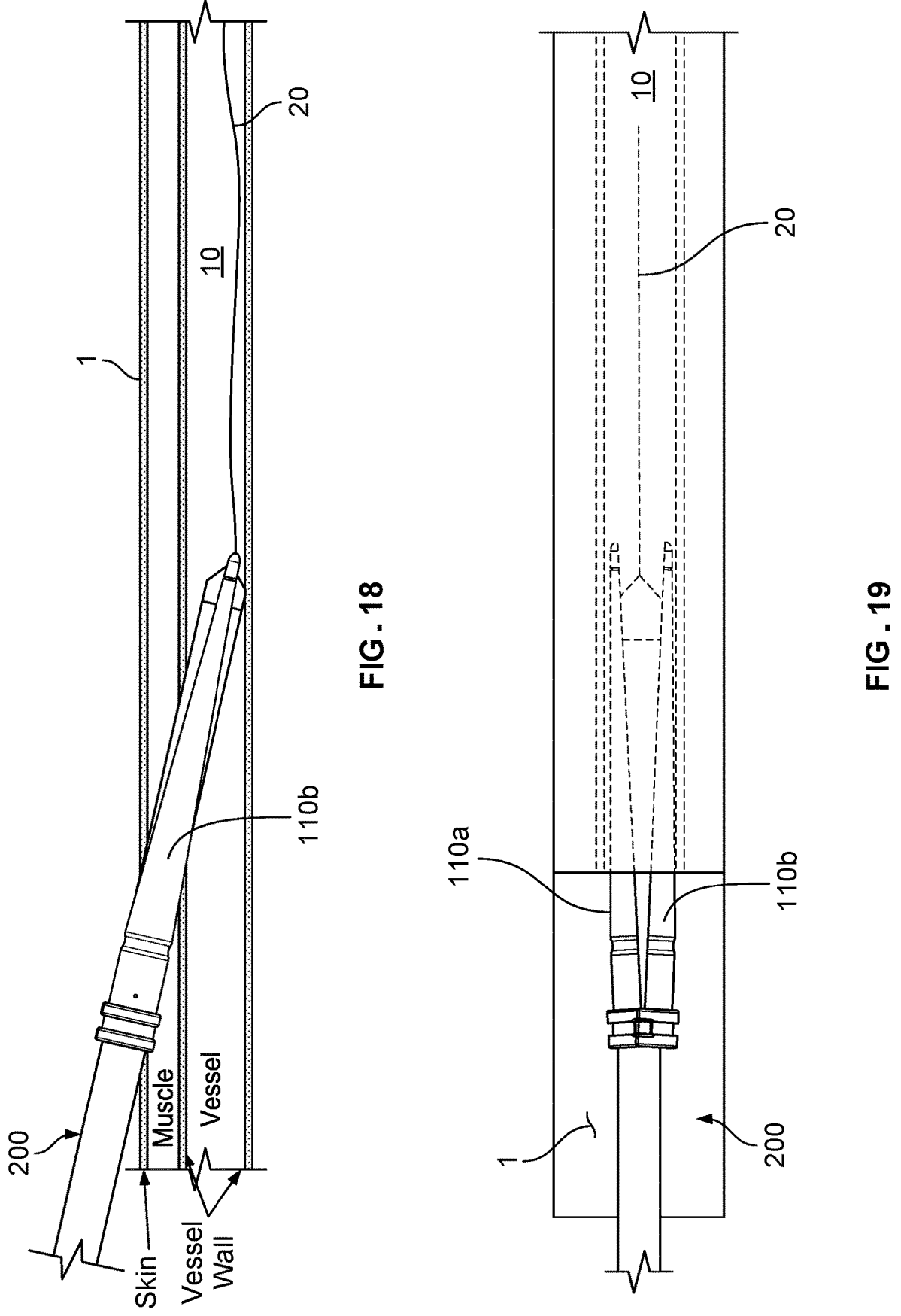
FIG. 18 shows the arrangement of FIG. 17 with the two halves of the conical tube of vascular dilating introducer device being split apart and the transvascular medical device system being advanced therethrough.
FIG. 19 shows a top view of the arrangement of FIG. 18.

FIGS. 18 and 19 show the advancement of the transvascular system 200 relative to the dilating introducer 100, resulting in the splitting of the two-piece conical tube 110. The advancement of the transvascular system 200 positions the distal end portion of the transvascular system 200 in the blood vessel 10. The transvascular system 200 can be advanced over the guidewire 20. In this manner, the dilating introducer 100 functions as an introducer sheath for the advancement of the transvascular system 200.

Figures 20, 21:
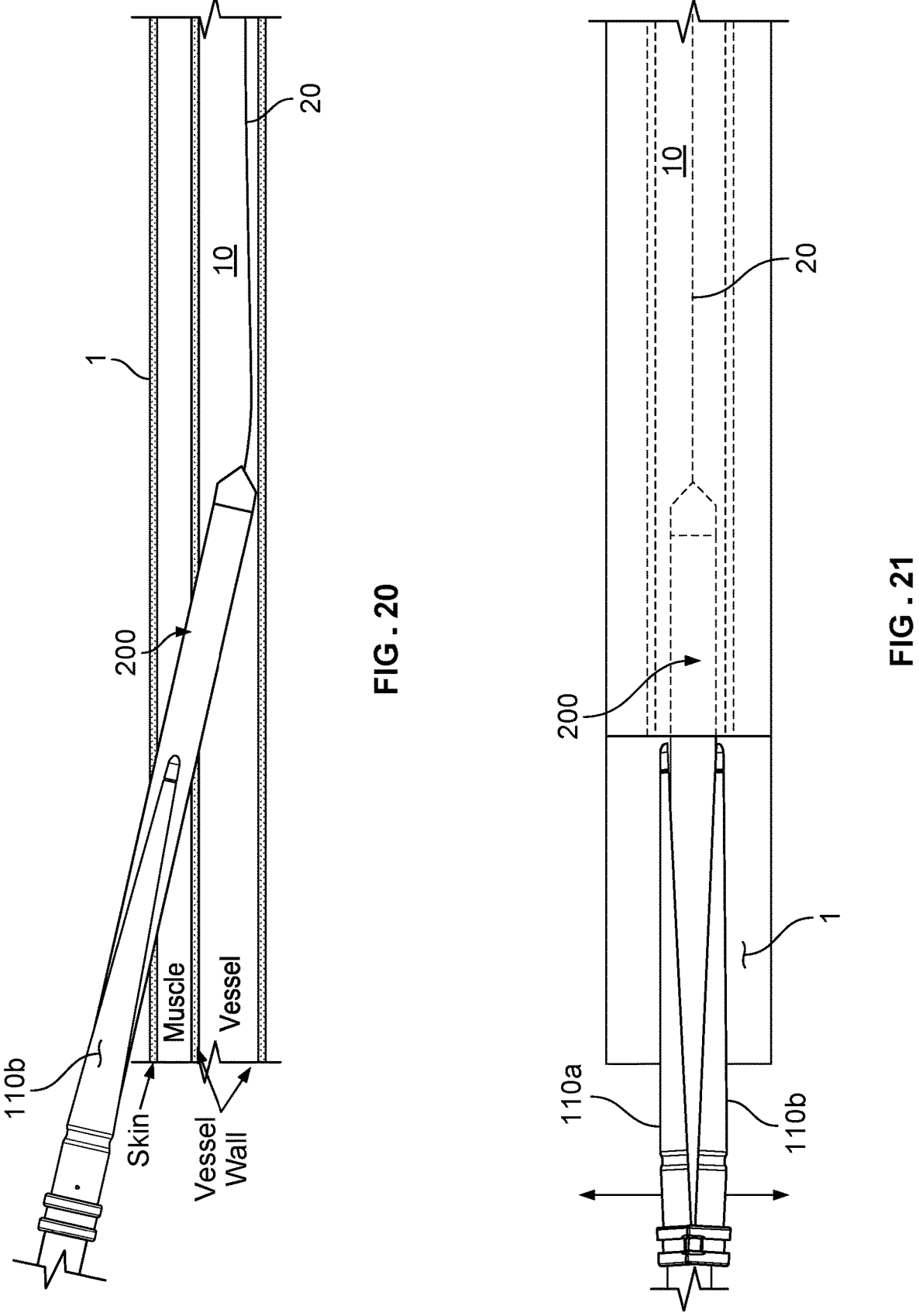
FIG. 20 shows the arrangement of FIG. 18 with the halves of the conical tube of vascular dilating introducer device being withdrawn from the patient while the transvascular medical device system remains in place.
FIG. 21 shows a top view of the arrangement of FIG. 20.

FIGS. 20 and 21 illustrate the withdrawal of the split dilating introducer 100 from the patient. The transvascular system 200 on the guidewire 20 is remaining with the distal end portions thereof in the blood vessel 10.

Figures 22, 23:
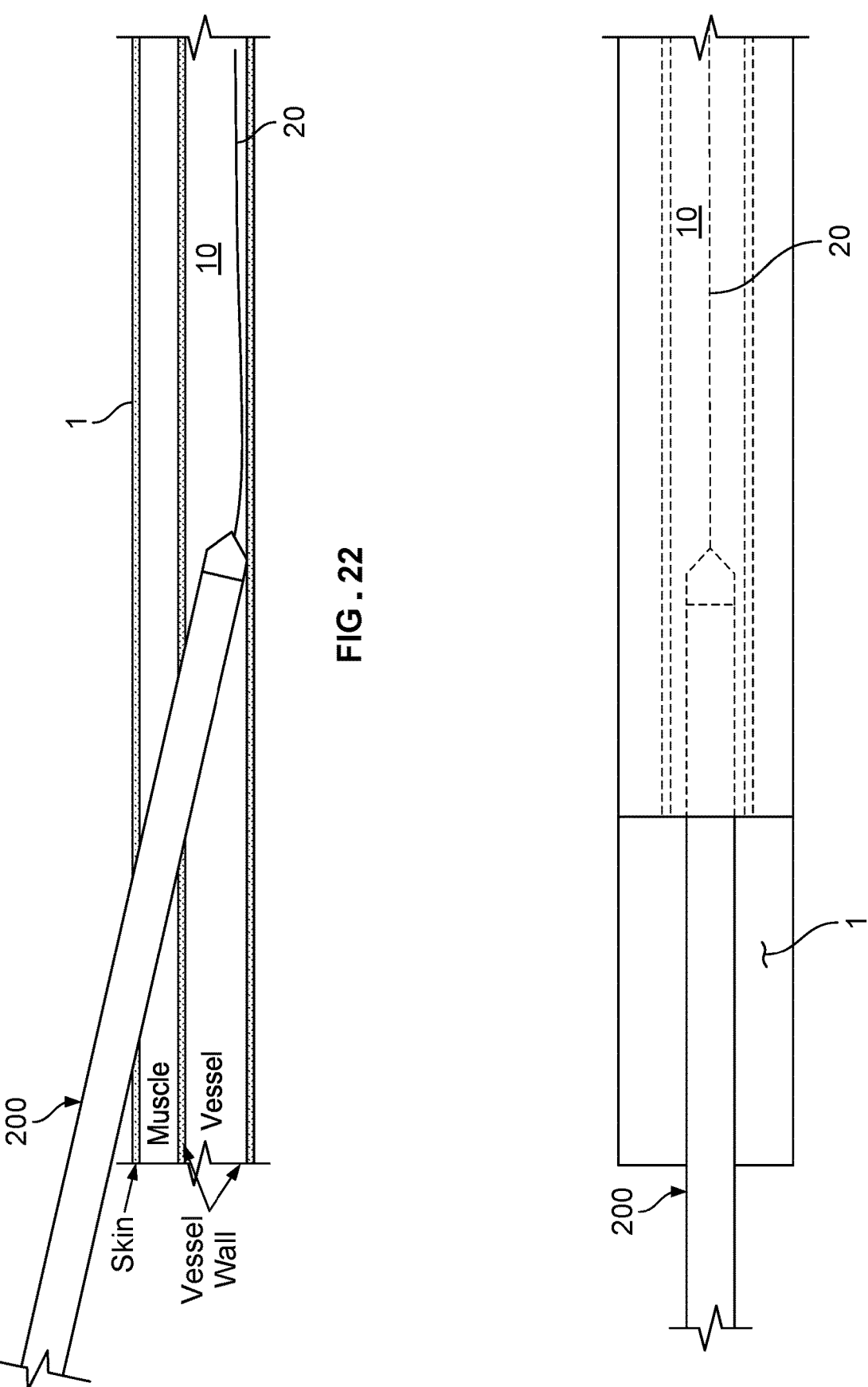
FIG. 22 shows the arrangement of FIG. 20 with the vascular dilating introducer device being completely withdrawn from the patient while the transvascular medical device system remains in place.
FIG. 23 shows a top view of the arrangement of FIG. 22.

FIGS. 22 and 23 illustrate the transvascular system 200 on the guidewire 20 remaining in position relative to the patient, with their distal end portions in the blood vessel 10. The dilating introducer 100 has been completely withdrawn. At this stage, the transvascular system 200 can be advanced via the blood vessel 10 as required for the performance of the medical procedure.

Figures 24, 25, 26:
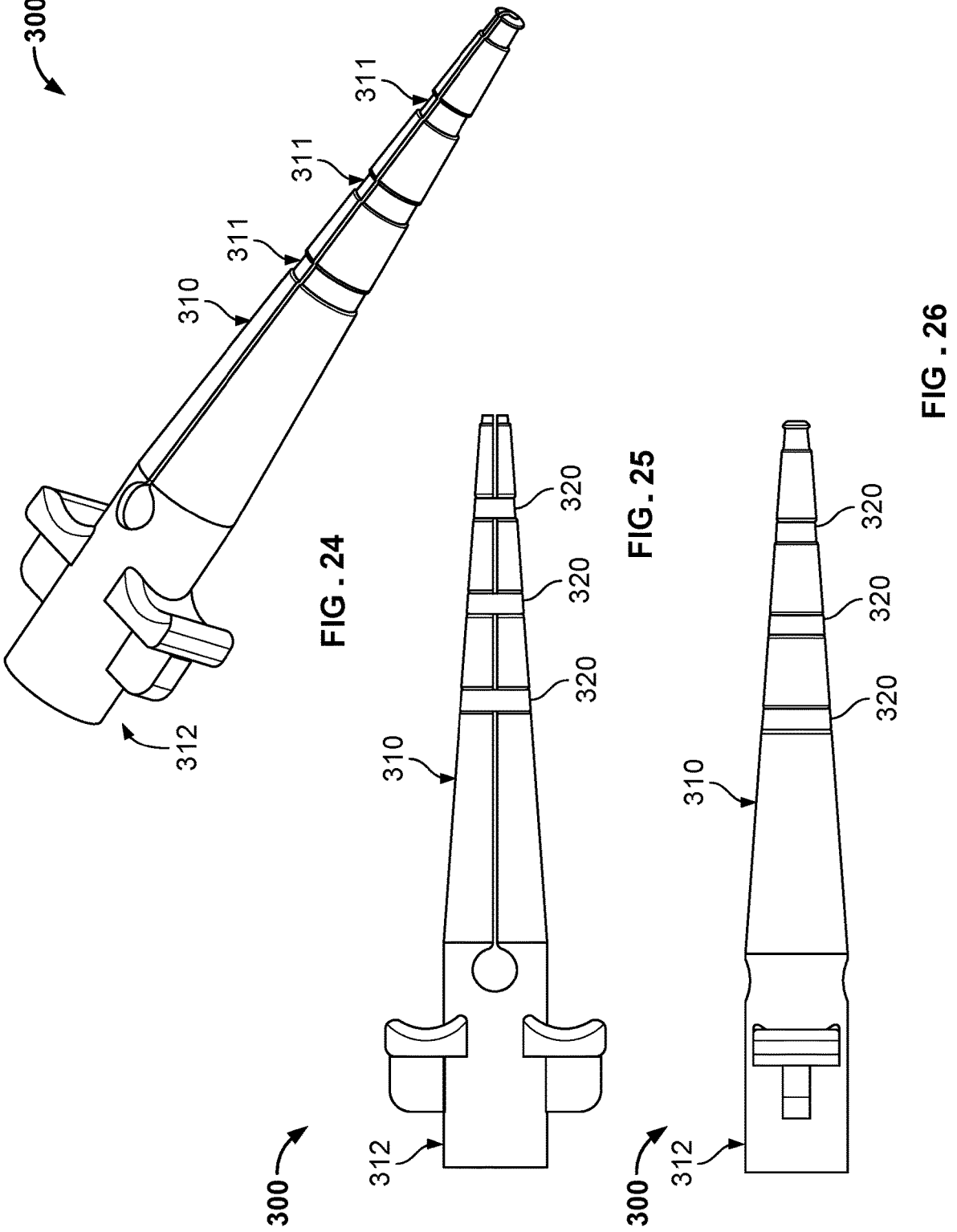
FIG. 24 is a perspective view of another example vascular dilating introducer device in accordance with some embodiments provided herein.
FIG. 25 is a top view of the vascular dilating introducer device of FIG. 24.
FIG. 26 is a side view of the vascular dilating introducer device of FIG. 24.

FIGS. 24-26 illustrate another dilating introducer 300. The dilating introducer 300 can be used by a medical clinician to percutaneously insert a transvascular medical device system into a blood vessel of a patient. The dilating introducer 300 serves to both dilate the tissue opening and/or blood vessel and also to introduce the transvascular medical device system into the blood vessel through the dilating introducer 300. That is, the dilating introducer 300 is a multifunctional device that can eliminate the need for a conventional introducer sheath that is commonly used when percutaneously inserting a transvascular medical device system into a blood vessel of a patient.

The dilating introducer 300 includes a conical tube 310, a hub 312 attached at a proximal end of the conical tube 310, and one or more elastic bands 320 coupled to the conical tube 310 to apply radially compressive hoop stress to the conical tube 310. The elastic bands 320 are shown in FIGS. 25 and 26, but are not shown in FIG. 24.

The conical tube 310 is longitudinally split into two portions (all the way to the distal tip). The two portions of the conical tube 310 that are split apart from each other can flex radially outward, away from each other, as a transvascular medical device system is advanced through the dilating introducer 300.

The conical tube 310 defines one or more annular recesses 311. The one or more annular recesses 311 receive the one or more elastic bands 320. In the depicted embodiment, there are three annular recesses 311 and three elastic bands 320. In some embodiments, there are one, two, four, or more than four annular recesses 311 and corresponding elastic bands 320.

The one or more elastic bands 320 are elastically stretchy. In some embodiments, the one or more elastic bands 320 are made of a material such as, but not limited to, a Pebax® elastomer or ChronoPrene™.

The elastic bands 320 function to bias the conical tube 310 to be configured in its conical shape as shown. However, when the transvascular medical device system is advanced through the dilating introducer 300, the elastic bands 320 stretch to allow the splaying apart of the two portions of the conical tube 310. In such a case, the two portions of the conical tube 310 flex radially outward away from each other in response to the passage of the larger diameter transvascular medical device system through the conical tube 310.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of introducing a catheter-based medical device into a blood vessel of a patient using a dilating introducer, the method comprising:

inserting a needle into the patient until a distal end portion of the needle is positioned in the blood vessel;

insert a guidewire through the needle and into the blood vessel;

removing the needle from the blood vessel;

advancing the dilating introducer over the guidewire until a distal end portion of the dilating introducer is in the blood vessel, wherein at least a portion of the catheter-based medical device is in a lumen of the dilating introducer during the advancing, wherein the dilating introducer comprises:

a conical tube comprising a first half that is releasably coupled to a second half;

a suture that releasably couples a distal end portion of the first half to a distal end portion of the second half; and a clip that releasably couples a proximal end portion of the first half to a proximal end portion of the second half;

while the distal end portion of the dilating introducer is in the blood vessel, advancing the catheter-based medical device over the guidewire and through the lumen of the dilating introducer to advance the catheter-based medical device into the vessel; and after the advancing of the catheter-based medical device over the guidewire and through the lumen of the dilating introducer to advance the catheter-based medical device into the vessel, removing the dilating introducer from the blood vessel, wherein the removing the dilating introducer from the blood vessel comprises:

removing the clip from the proximal end portions of the first half and the second half; and removing the suture from the distal end portions of the first half and the second half.

2. The method of claim 1, wherein the removing the dilating introducer from the blood vessel comprises longitudinally splitting the dilating introducer into the first half and the second half as separate pieces.

3. The method of claim 1, wherein, when the dilating introducer is advanced into the blood vessel, the dilating introducer is a single component, and wherein the method of using the dilating introducer is performed without using: (i) a dilator and (ii) an introducer sheath as two separate components.

4. The method of claim 1, wherein a distal end portion of the catheter-based medical device is in the vessel prior to the removing the dilating introducer from the blood vessel.

5. The method of claim 1, wherein the catheter-based device is a prosthetic heart valve coupled on a system of delivery catheters.

6. The method of claim 1, wherein the suture is connected to the clip.

* * * * *